United States Patent [19]

Boehmer

[11] Patent Number: 4,827,973

[45] Date of Patent: May 9, 1989

[54] ONE WAY FLOW VALVE

[75] Inventor: Dennis A. Boehmer, Xenia, Ohio

[73] Assignee: Vernay Laboratories, Inc., Yellow Springs, Ohio

[21] Appl. No.: 211,790

[22] Filed: Jun. 27, 1988

[51] Int. Cl.⁴ .................. F16K 15/14; F16K 37/00
[52] U.S. Cl. ................ 137/512.15; 137/512.4; 137/854; 137/559
[58] Field of Search ............ 137/512.15, 512.4, 852, 137/854, 855, 559

[56] References Cited

U.S. PATENT DOCUMENTS

| Re. 27,399 | 6/1972 | Urso | 137/512.15 |
|---|---|---|---|
| 2,688,978 | 9/1954 | Von Wangenheim | 137/512.15 |
| 2,800,920 | 7/1957 | Smith | 137/512.15 |
| 2,954,048 | 9/1960 | Rychlik | 137/512.15 |
| 3,022,796 | 2/1962 | Cummings | 137/454.6 |
| 3,037,522 | 6/1962 | Millan | 137/512.15 X |
| 3,066,695 | 12/1962 | Allen | 137/512.15 |
| 3,312,237 | 4/1967 | Mon et al. | 137/512.15 |
| 3,412,754 | 11/1968 | Schou et al. | 137/512.15 |
| 3,568,977 | 3/1971 | Nelson | 137/512.15 X |
| 3,889,710 | 6/1975 | Brost | 137/512.15 |
| 3,916,948 | 11/1975 | Benjamin | 137/559 X |
| 4,191,211 | 3/1980 | Walker | 137/512.15 |
| 4,210,174 | 7/1980 | Eross | 137/559 X |
| 4,222,407 | 9/1980 | Ruschke et al. | 137/512.15 |
| 4,535,818 | 8/1985 | Duncan et al. | 137/846 |
| 4,535,819 | 8/1985 | Atkinson et al. | 137/846 |
| 4,566,493 | 1/1986 | Edwards et al. | 137/846 |

Primary Examiner—John Rivell
Attorney, Agent, or Firm—Biebel, French & Nauman

[57] ABSTRACT

A valve assembly is disclosed which allows fluid flow in a first direction and prevents fluid flow in a second, opposite direction comprising a valve housing having an upper section, a lower section and a longitudinal axis therethrough. The upper section includes an inlet end and a pair of opposite facing walls, generally equally spaced from the longitudinal axis and arranged in a diverging relationship away from the inlet end. The upper section further includes opposite facing walls, generally equally spaced from the longitudinal axis and generally perpendicular to the diverging walls. The inner surfaces of each diverging wall includes an outer perimeter and a concave surface extending inwardly from the perimeter. A flow regulator and valve support is disposed longitudinally within the upper section of the valve housing for supporting an elastomeric valve member within the upper section. The valve member comprises two mutually diverging sealing members to provide substantially linear sealing contact with the perimeter of the diverging walls of the upper section of the valve housing.

22 Claims, 1 Drawing Sheet

ONE WAY FLOW VALVE

BACKGROUND OF THE INVENTION

The present invention relates generally to flow regulation apparatus, and more particularly, to a valve assembly adapted to permit substantially free flow through the valve in a first direction, while preventing flow through the valve in a second, opposite direction.

The numerous uses of one way flow valves are well recognized. Such valves are particularly useful in the medical field such as in the performing of medical infusions.

One of the requirements for such valves is that the valves must offer little resistance to fluid flow in one direction but will completely stop fluid flow in the opposite direction. Many prior art valves do not operate or will not fully open at low inlet pressures. Other prior art valves will have a tendency to leak. This tendency to leak increases as the back pressure acting on the valve is lowered acting on the valve.

Other requirements for such valves is that they must be able to be economically manufactured, light in weight, simple in construction, and easy to use. Many prior art valves require that extremely close mechanical tolerances be maintained to prevent back flow during the period in which the valves are closed. The requirement of very close tolerances results in a significant increase in the cost of manufacturing the valves.

An additional requirement of such valves is their ability to purge air. Many prior art valves such as those using a disc or plate for sealing, tend to trap air. This air needs to be purged before intravenous infusion to reduce the possibility of an embolism occurring in the patient.

Accordingly, a need exists for a valve assembly allowing fluid flow in a first direction and preventing fluid flow in a second, opposite direction which is economical to manufacture, easy to use, and can operate reliably, efficiently, and safely on a variety of fluids.

SUMMARY OF THE INVENTION

The present invention is a valve assembly allowing fluid flow in a first direction and for preventing fluid flow in a second, opposite direction comprising a valve housing having an upper section, a lower section and a longitudinal axis therethrough. The upper section includes an inlet end and a pair of opposite facing walls, generally equally spaced from the longitudinal axis and arranged in a diverging relationship away from the inlet end. The upper section further includes opposite facing walls, generally equally spaced from the longitudinal axis and generally perpendicular to the diverging walls, and an inlet port in flow communication with the inlet end. The inner surfaces of each diverging wall includes an outer perimeter and a concave surface extending inwardly from the perimeter.

A flow regulator and valve support is disposed longitudinally within the upper section of the valve housing for supporting an elastomeric valve member within the upper section. The valve member comprises an apex cooperating with the flow regulator and valve support to position and support the valve member, and two mutually diverging, generally rectangularly shaped sealing members. The sealing members are equally spaced from the longitudinal axis and provide substantially linear sealing contact with the perimeter of the diverging walls of the upper section of the valve housing.

Differential fluid pressure in the valve housing tending to produce fluid flow through the valve will deflect the sealing members of the valve member inwardly out of contact with the perimeter of the diverging walls of the upper section of the valve housing, thereby allowing substantially unrestricted fluid flow through the valve. Differential fluid pressure in the valve housing tending to produce generally opposite flow through the valve will deflect the sealing members of the valve member outwardly into contact with the perimeter of the diverging walls of the upper section of the valve housing, thereby preventing opposite flow.

The primary object of this invention, therefore, is to provide a valve assembly which will offer little resistance to fluid flow in a first direction but will completely stop fluid flow in a second, opposite direction; to provide a valve assembly which is light in weight, simple in construction, economical to manufacture and efficient in operation; to provide a valve assembly which naturally purges itself of air; to provide a valve assembly which will provide little flow restriction during low pressure, forward flow conditions while being capable of providing an effective seal during low and high back pressure conditions; and to provide a valve assembly which is less susceptible to clogging and leaking due to trapped solid particles.

Other objects and advantages of the invention will be apparent from the following description, the accompanying drawings and the appended claims.

DESCRIPTION OF THE PREFERRED EMBODIMENT

Figure 1:
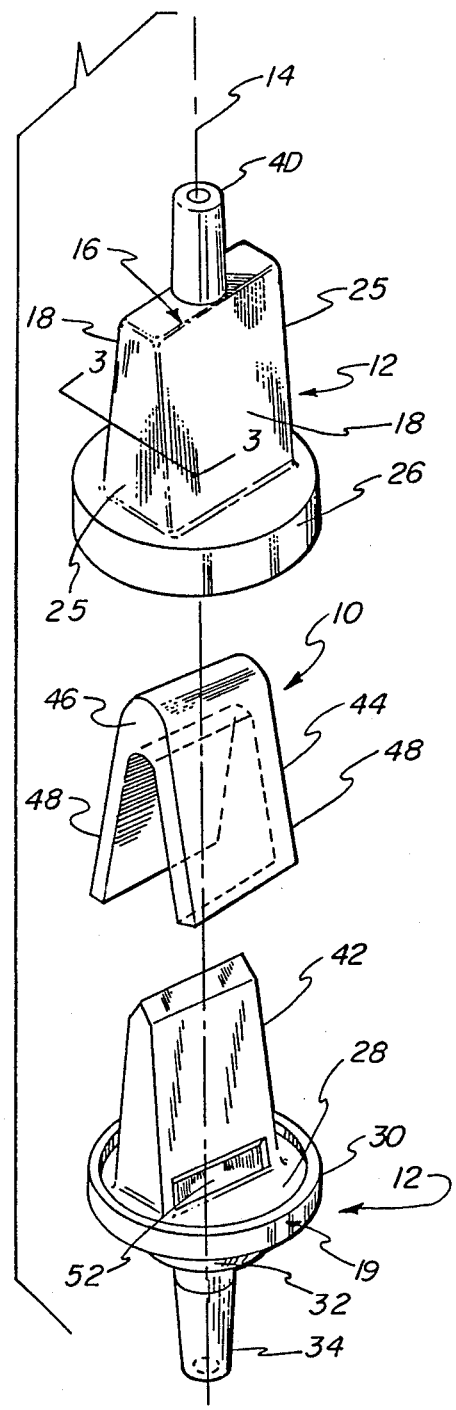
FIG. 1. is a perspective exploded view of a preferred embodiment of the one way check valve of the present invention.

A valve assembly, generally designated 10, is shown in the drawing in greater detail having a housing 12 and a longitudinal axis 14. Valve housing 12 comprises an upper section 16 having two opposite facing, diverging walls 18 equally spaced from the longitudinal axis 14. As shown in FIGS. 2 and 3, diverging inner surfaces 20 of diverging walls 18 each include an outer perimeter 22 and concave surface 24 extending inwardly from outer perimeter 22. The upper section 16 of valve housing 12 further includes oppositely facing walls 25 (FIG. 1) which are generally equally spaced from the longitudinal axis 14 and are substantially perpendicular to diverging walls 18. Upper section 16 terminates in a bottom ring section 26 for sealing engagement with a lower valve housing section 19.

Figure 2:
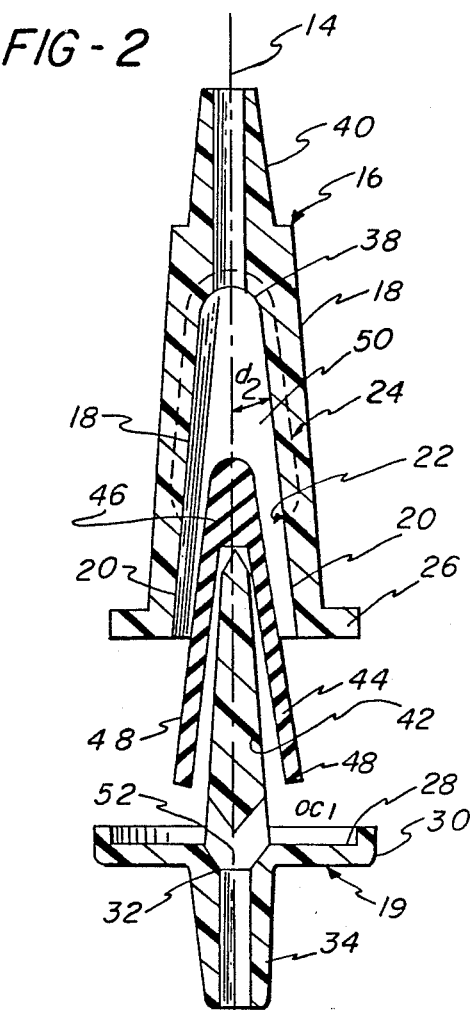
FIG. 2 is a sectional view of the one way check valve of FIG. 1 shown in a partially assembled state.
Figure 3:
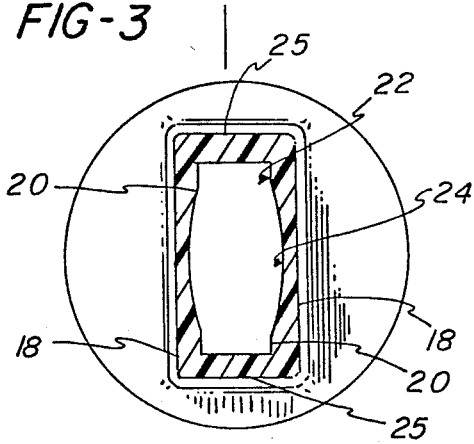
FIG. 3 is a top sectional view of the valve assembly taken along line 3—3 of FIG. 1 showing the concave inner surfaces of the diverging walls.

As shown in FIGS. 1 and 2, lower section 19 comprises a one-piece casing having an axially facing recess 28 and end flange 30 circumferentially positioned about longitudinal axis 14 and adapted to mate with bottom ring section 26 of upper section 16 and to be easily sealed using an ultrasonic welding technique.

Located longitudinally outwardly from recess 28 is an outlet end 32. An outlet port 34 communicates with outlet end 32 for connecting valve 10 to a suitable fluid receiving line (not shown). The upper section 16 of valve housing 12 further comprises an inlet end 38 and an inlet port 40 extending longitudinally outwardly therefrom for connecting valve 10 to a suitable fluid supply source (not shown).

A flow regulator and valve support 42 extends longitudinally from recess 28 into valve housing 12. Mounted on support 42 and disposed longitudinally within upper section 16 of valve housing 12 is an elastomeric valve member 44 having a center apex 46 and two generally rectangularly shaped inclined sealing members 48 extending outwardly therefrom.

Elastomeric valve member 44 is constructed so that the included angle $\alpha_1$, between the longitudinal axis 14 of valve 10 and the elastomeric valve member 44 (prior to being inserted into valve housing 12 is greater than the included angle $\alpha_2$ between the longitudinal axis 14 of the valve 10 and the outer perimeter 22 of inner surface 20 of each diverging wall 18. When valve member 44 is seated into housing cavity 50, defined by diverging walls 18 and oppositely facing walls 25, elastomeric sealing members 48 are deflected inwardly and are biased into substantially linear sealing contact with outer perimeters 22.

In use, valve member 44 responds to differential fluid pressure in housing cavity 50 between fluid inlet end 38 and fluid outlet end 32. Due to the relatively large surface area of sealing members 48, a slightly greater fluid pressure at the inlet end 38 tending to produce flow in a first direction through the valve will deflect sealing members 48 inwardly out of sealing contact with outer perimeters 22 of diverging walls 18, allowing substantially unrestricted fluid flow through the valve. A change in the differential fluid pressure tending to produce flow in a second opposite direction will immediately allow elastomeric sealing members 44 to deflect back into contact with outer perimeters 22 of diverging walls 18, thereby forming a seal and preventing opposite flow.

In addition to supporting valve member 44, flow regulator and valve support 42 has fluid flow channels 52 or other equivalent functional means, which are presized to regulate flow out of the valve and to ensure a predetermined amount of steady turbulent free flow enters into the fluid receiving line.

It will be apparent that concave surfaces 24 of diverging walls 18 are adapted to help trap solid particles, which maybe present in the fluid, thereby reducing the possibility of fluid flow restrictions or seal leakage. In addition, concave surfaces 24 are adapted to provide a generally adequate flow area and even pressure distribution along sealing members 48 of valve member 44 to prevent excessive distortion and destruction of sealing members 48 during high inlet flow and pressure conditions. Furthermore, the large contact and sealing surface areas provided by outer perimeters 22 will prevent excessive distortion and destruction of sealing members 48 if the reverse back pressure differential becomes large.

It will also be apparent that the flutter type motion of sealing members 48 will reduce the possibility of trapping air in the valve. In addition, it will be apparent that valve housing 12 may be constructed sufficiently narrow such that capillary attraction of the fluid will function to naturally purge any existing air pockets in the valve 10.

In a preferred embodiment of the invention, valve housing 12 is constructed easily and inexpensively using a suitable molded plastic. The elastomeric valve member 44 is easily molded or cut from an extrusion having the specific physical qualities and required thickness. Apex 46 is formed relatively thick for enduring repeated flexure.

In a preferred embodiment of the invention, valve 10 is formed of a radiation sterilizable clear plastic material for ease in observing air purging of the valve and for added safety for medical use.

While the form of apparatus herein described constitutes preferred embodiments of this invention, it is to be understood that the invention is not limited to these precise forms of apparatus, and that changes may be made therein without departing from the scope of the invention which is defined in the appended claims.

What is claimed is:

1. A check valve allowing fluid flow in a first direction and preventing fluid flow in a second direction comprising:
    a housing having an upper section and a longitudinal axis therethrough, said upper section having diverging walls;
    an elastomeric valve member disposed longitudinally within said upper section having two sealing members generally equally spaced and diverging generally downwardly and away from said longitudinal axis for substantially linear sealing contact with said diverging walls of said upper section; and
    a lower section adapted to mate with said upper section.

2. A check valve of claim 1 wherein said upper section of said housing includes a fluid inlet port having means for connecting said valve to a suitable fluid supply.

3. A check valve of claim 1 wherein said lower section includes means for connecting said valve to a suitable fluid receiving line.

4. A check valve of claim 1 wherein said elastomeric valve member includes an apex adapted for enduring repeated flexure.

5. A check valve of claim 1 wherein said housing is formed of radiation sterilizable plastic material.

6. A check valve of claim 1 wherein said valve member is formed of radiation sterilizable elastomeric material.

7. A check valve of claim 6 wherein said valve housing includes an inlet port and a ring section coaxially located about said longitudinal axis for mating with said outlet port.

8. A check valve allowing fluid flow in a first direction and preventing fluid flow in a second generally opposite direction comprising:
    a valve housing having a longitudinal axis and diverging walls generally equally spaced about said longitudinal axis;
    a flow regulator and valve support disposed longitudinally within said housing;
    an elastomeric valve member disposed longitudinally within said valve housing having an apex cooperating with said flow regulator and valve support to position and support said valve member, said valve member including two diverging sealing members generally equally spaced from said longitudinal axis and forming an acute angle with said longitudinal axis for providing substantially linear sealing contact with said diverging walls; and
    a lower section having an outlet port and adapted to mate with said housing.

9. A check valve of claim 8 wherein differential fluid pressure in said housing tending to produce fluid flow in the first direction through said valve will deflect said sealing members inwardly out of contact with said diverging walls allowing substantially unrestricted fluid flow through the valve, and wherein differential fluid pressure in said housing tending to produce a second generally opposite flow through the valve will deflect said sealing members outwardly into contact with said diverging walls preventing said generally opposite flow.

10. A check valve of claim 8 wherein said flow regulator and valve support is adapted for supporting said valve member and for regulating flow out of the valve to ensure steady turbulent free fluid flow into a fluid receiving line.

11. A check valve of claim 8 wherein said valve housing is formed of radiation sterilizable plastic material.

12. A check valve of claim 8 wherein said valve member are formed of radiation sterilizable elastomeric material.

13. A check valve of claim 8 wherein the valve is sufficiently narrow to naturally purge air using capillary attraction of the fluid.

14. A check valve of claim 8 wherein said apex is adapted for enduring repeated flexure.

15. A check valve allowing fluid flow in a first direction and preventing fluid flow in a second generally opposite direction comprising:
   a valve housing having a longitudinal axis and diverging walls equally spaced about said longitudinal axis;
   a flow regulator and valve support disposed longitudinally within said housing;
   an elastomeric valve member disposed longitudinally within said valve housing having an apex cooperating with said flow regulator and valve support to position and support said valve member, said valve member including two diverging sealing members equally spaced from said longitudinal axis and providing substantially linear sealing contact with said diverging walls; and
   a lower section having an outlet port and adapted to mate with said housing;
   wherein said sealing members are generally rectangular shaped.

16. A check valve allowing fluid flow in a first direction and preventing fluid flow in a second generally opposite direction comprising:
   a valve housing having an upper section, a lower section, and a longitudinal axis therethrough, said upper section including an inlet end and a pair of walls generally equally spaced from said longitudinal axis and arranged in a diverging relationship away from said inlet end, wherein said diverging walls each comprising an inner surface having an outer perimeter and a concave surface extending inwardly from said outer perimeter, and wherein said upper section further comprising generally oppositely facing walls, generally equally spaced and parallel to said longitudinal axis and generally perpendicular to said diverging walls;
   a flow regulator and valve support disposed longitudinally within said upper section; and
   an elastomeric valve member disposed longitudinally within said upper section having an apex cooperating with said flow regulator and valve support to position and support said valve member, and two mutually diverging, sealing members equally spaced from said longitudinal axis for substantially linear sealing contact with said outer perimeter.

17. A check valve of claim 16 wherein said lower section includes an outlet port and is adapted to mate with said upper section.

18. A check valve of 16 wherein said sealing members are generally rectangularly shaped.

19. A check valve of claim 16 wherein said apex is adapted for enduring repeated flexure.

20. A check valve of claim 16 wherein said valve housing is formed of radiation sterilizable plastic material.

21. A check valve of claim 16 wherein said valve housing is formed of radiation sterilizable clear plastic material.

22. A check valve of claim 16 wherein said valve member is formed of radiation sterilizable elastomeric material.

* * * * *